(12) United States Patent
Rein

(10) Patent No.: US 12,152,871 B2
(45) Date of Patent: Nov. 26, 2024

(54) METHOD AND APPARATUS FOR DETERMINING A VERTICAL POSITION OF A HORIZONTALLY EXTENDING INTERFACE BETWEEN A FIRST COMPONENT AND A SECOND COMPONENT

(71) Applicant: Roche Diagnostics Operations, Inc., Indianapolis, IN (US)

(72) Inventor: Michael Rein, Fellbach (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 751 days.

(21) Appl. No.: 17/110,451

(22) Filed: Dec. 3, 2020

(65) Prior Publication Data

US 2021/0172725 A1    Jun. 10, 2021

(30) Foreign Application Priority Data

Dec. 10, 2019    (EP) .................................... 19214877

(51) Int. Cl.
 *G01B 11/02*     (2006.01)
 *G01N 15/04*     (2006.01)
 (Continued)

(52) U.S. Cl.
 CPC ........... *G01B 11/028* (2013.01); *G01N 15/05* (2013.01); *G01N 33/491* (2013.01);
 (Continued)

(58) Field of Classification Search
 CPC .... G01B 11/028; G01N 15/05; G01N 33/491; G01N 35/00732; G01N 2015/045;
 (Continued)

(56) References Cited

U.S. PATENT DOCUMENTS 6,157,894 A     12/2000   Hess et al.
9,253,448 B1    2/2016    Wang et al.
(Continued)

FOREIGN PATENT DOCUMENTS

CN    107797141 A    8/2018
CN    108957463      12/2018
(Continued)

OTHER PUBLICATIONS

Wikipedia, "Kalman Filter," 2023 (Year: 2023).*
(Continued)

*Primary Examiner* — Matthew G Marini
*Assistant Examiner* — Leo T Hinze
(74) *Attorney, Agent, or Firm* — Woodard, Emhardt, Henry, Reeves & Wagner, LLP

(57) ABSTRACT

A method for determining a vertical position of a horizontally extending interface between first and second components is presented. The first and second components are contained in a laboratory sample container in layers vertically separated from each other. The method comprises generating first data, generating second data in the form of picture data of the laboratory sample container containing the first and second components, determining a first probability distribution function in response to the first data, determining a second probability distribution function in response to the second data, and determining the vertical position of the horizontally extending interface depending on the first and second probability distribution functions. The first data depend on the vertical position of the horizontally extending interface. The first and second probability distribution functions assign a probability of the presence of the horizontally extending interface to a vertical position.

10 Claims, 5 Drawing Sheets

(51) Int. Cl.
*G01N 15/05* (2006.01)
*G01N 33/49* (2006.01)
*G01N 35/00* (2006.01)

(52) U.S. Cl.
CPC . *G01N 35/00732* (2013.01); *G01N 2015/045* (2013.01); *G01N 2035/00495* (2013.01)

(58) Field of Classification Search
CPC .......... G01N 2035/00495; G01N 2035/00752; G01N 2035/1025; G01N 35/1016; G01N 15/042; G01N 21/13; G01N 33/48; G01N 2035/0493; G06F 17/18; G06F 18/24155; G06F 18/257; G06T 7/277
See application file for complete search history.

(56) References Cited

U.S. PATENT DOCUMENTS

| | | | |
|---|---|---|---|
| 2011/0268329 A1* | 11/2011 | Pronkine | G01F 23/804 382/128 |
| 2014/0233042 A1* | 8/2014 | Klinec | G01F 23/2921 356/614 |
| 2018/0321386 A1 | 11/2018 | Bosetti et al. | |
| 2019/0383793 A1* | 12/2019 | Sugiyama | G01N 35/1009 |

FOREIGN PATENT DOCUMENTS

| | | |
|---|---|---|
| EP | 1731922 | 12/2006 |
| EP | 2770317 A1 | 8/2014 |
| EP | 3467452 A1 | 4/2019 |
| EP | 3149492 B1 | 6/2020 |
| JP | 2014-6094 A | 1/2014 |
| WO | 2017/132166 A1 | 8/2017 |
| WO | 2017/132171 A1 | 8/2017 |
| WO | 2018/127996 A1 | 7/2018 |
| WO | 2019/018313 A1 | 1/2019 |

OTHER PUBLICATIONS

European Search Report issued May 28, 2020, in Application No. EP 19214877.3, 2 pp.
Sun et al. "Bayesian estimation method for multi-source data fusion", Jounral of Qilu University if Technology, vol. 32, issue 01, Feb. 28, 2018.

* cited by examiner

METHOD AND APPARATUS FOR DETERMINING A VERTICAL POSITION OF A HORIZONTALLY EXTENDING INTERFACE BETWEEN A FIRST COMPONENT AND A SECOND COMPONENT

CROSS-REFERENCE TO RELATED APPLICATIONS

This application claims priority to EP 19214877.3, filed Dec. 10, 2019, which is hereby incorporated by reference.

BACKGROUND

The present disclosure generally relates to a method and an apparatus for determining a vertical position of a horizontally extending interface between a first component and a second component, wherein the first component and the second component are contained in a laboratory sample container in layers that are vertically separated from each other.

There is a need for a method and an apparatus for determining a vertical position of a horizontally extending interface between a first component and a second component having improved characteristics compared to prior art solutions.

SUMMARY

According to the present disclosure, an apparatus and method for determining a vertical position ($z\_pv$) of a horizontally extending interface between a first component and a second component are presented. The first component and the second component can be contained in a laboratory sample container in layers that are vertically separated from each other. The method can comprise generating first data. The first data can depend on the vertical position ($z\_pv$) of the horizontally extending interface. The method can also comprise generating second data in the form of picture data of the laboratory sample container containing the first component and the second component and determining a first probability distribution function (f1) in response to the first data. The first probability distribution function (f1) can assign a probability of the presence of the horizontally extending interface to a vertical position. The method can also comprise determining a second probability distribution function (f2) in response to the second data. The second probability distribution function (f2) can assign a probability of the presence of the horizontally extending interface to a vertical position (z). The method can also comprise determining the vertical position ($z\_pv$) of the horizontally extending interface depending on the first probability distribution function (f1) and on the second probability distribution function (f2).

Accordingly, it is a feature of the embodiments of the present disclosure to provide for a method and an apparatus for determining a vertical position of a horizontally extending interface between a first component and a second component having improved characteristics compared to prior art solutions. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
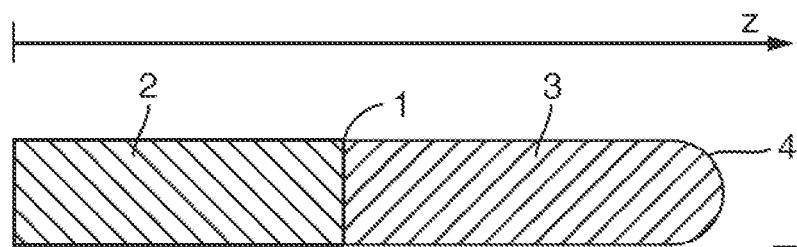
FIG. 1a illustrates a test sample container containing a first test component and a second test component in layers that are vertically separated from each other, wherein a horizontally extending interface is formed between the first test component and the second test component according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

By use of the inventive method, a vertical position of an interface between a first component and a second component may be determined. The first component and the second component can be contained in a laboratory sample container in layers that are vertically separated from each other, if a longitudinal axis of the laboratory sample container is substantially perpendicular to a horizontal plane, i.e., when the laboratory sample container is aligned such that a laboratory sample contained in the laboratory sample container may be processed, e.g., pipetted and the like.

The laboratory sample container may be embodied as a conventional transparent laboratory sample container or as a laboratory sample tube used in automated laboratory instrumentation. The method may be intended to detect horizontal interfaces between different layers of a centrifuged blood sample such as interfaces between a serum or plasma layer and either a separation medium layer or a cruor (blood cell) layer.

The method can comprise the following steps. First data can be generated. The first data can depend on the vertical position of the horizontally extending interface. The first data may e.g., be formed as a set of digital data words. For a given vertical position, a digital data word of the set of digital data words can be assigned. The digital data word can depend on properties of the components contained in the laboratory sample container at the given vertical position.

Second data can be generated in the form of digital picture data of the laboratory sample container containing the first component and the second component. The picture data may e.g., be embodied as raw picture data generated by a conventional image sensor or may be embodied as picture data formed by compressing the raw data, e.g., in a jpg-format and the like. The picture data may comprise color information of the laboratory sample container containing the first component and the second component.

A first probability distribution function can be computed in response to the first data. The first probability distribution function can be assign a probability of the presence/occurrence of the horizontally extending interface to a vertical position.

A second probability distribution function can be computed in response to the second data. The second probability distribution function can be assign a probability of the presence of the horizontally extending interface to a vertical position. To determine or compute the second probability distribution function, conventional image processing methods may be used. By the image processing methods e.g., properties of the first component, properties of the second component, properties of the laboratory sample container, and/or properties of labels/barcodes attached to the laboratory sample container may be determined. The second probability distribution function may be computed or determined based on the properties of the first component, the properties of the second component, the properties of the laboratory sample container, and/or the properties of labels/barcodes attached to the laboratory sample container.

Finally, the vertical position of the horizontally extending interface can be computed depending on the first probability distribution function and on the second probability distribution function.

According to an embodiment, the first data can be generated by sensing a transmittance through the laboratory sample container at different vertical positions. The first data, for example, may be, for this case, formed as a set of digital data words. For a given vertical position, a digital data word of the set of digital data words can correspond to a transmittance at the given vertical position. The transmittance may be sensed for different wavelengths. The first probability distribution function may e.g., be determined based on the disclosure of EP 2 770 317 A1, which is hereby incorporated by reference.

According to an embodiment, the vertical position of the horizontally extending interface can be determined depending on the first probability distribution function and on the second probability distribution function by combining the first probability distribution function and the second probability distribution function based on Bayes' theorem, Dempster-Shafer theory, and/or Kalman filtering. Reference is made insofar to the relevant technical literature.

According to an embodiment, the method can further comprise providing a test sample container. A first test component and a second test component can be contained in the test laboratory sample container in layers that are vertically separated from each other. The method can further comprise determining a vertical position of a horizontally extending interface between the first test component and the second test component a number of times, e.g., 1000 to 100000 times, determining a first frequency distribution of the determined vertical positions, and determining the first probability distribution function in response to the first data and in response to the first frequency distribution. The first data may e.g., be used to compute a likely vertical position of the horizontally extending interface between the first component and the second component based on the disclosure of EP 2 770 317 A1. The first probability distribution function can then be determined by centering the first frequency distribution at the computed (hypothetical) vertical position.

According to an embodiment, the method can further comprise providing a test sample container having a label attached to the test sample container, determining geometrical properties of the label, e.g., a vertical position of one boundary of the label, a number of times, e.g., 1000 to 100000 times, determining a second frequency distribution of the determined geometrical properties, and determining the second probability distribution function in response to the second data and in response to the second frequency distribution. The second data may e.g., be used to compute vertical positions of vertical boundaries of an attached label, e.g., by image processing. Then, the second frequency distribution may be centered at the vertical positions of the vertical boundaries of the attached label. The resulting function may then be used to determine the second probability distribution function.

According to an embodiment, the method can further comprise providing a test sample container having a barcode label attached to the test sample container, determining geometrical properties of the barcode label a number of times, determining a third frequency distribution of the determined geometrical properties, and determining the second probability distribution function in response to the second data and in response to the third frequency distribution.

According to an embodiment, the method can further comprise generating the second data comprising color information. The second probability distribution function can be determined in response to the color information.

According to an embodiment, the method can further comprise pipetting the first component and/or the second component in response to the determined vertical position of the horizontally extending interface.

An apparatus can be configured to determine a vertical position of a horizontally extending interface between a first component and a second component. The first component and the second component can be contained in a laboratory sample container in layers that are vertically separated from each other. The apparatus can comprise a measurement unit configured to generate first data. The first data can depend on the vertical position of the horizontally extending interface. The apparatus can also comprise a digital camera configured to generate second data in the form of picture data of the laboratory sample container containing the first component and the second component and a processing unit configured to determine a first probability distribution function in response to the first data. The first probability distribution function can assign a probability of the presence of the horizontally extending interface to a vertical position. The processing unit can also be configured to determine a second probability distribution function in response to the second data. The second probability distribution function can assign a probability of the presence of the horizontally extending interface to a vertical position. The processing unit can also be configured to determine the vertical position of the horizontally extending interface depending on the first probability distribution function and on the second probability distribution function.

According to an embodiment, the measurement unit can be configured to generate the first data by sensing a transmittance through the laboratory sample container at different vertical positions. The measurement unit may be embodied as disclosed in EP 2 770 317 A1.

FIG. 1a depicts a test sample container 4, i.e., a laboratory sample container used for training purposes, containing a first test component 2, e.g., in the form of blood serum or an artificial equivalent, and a second test component 3 in the form of a gel in layers that are vertically separated from each other. A horizontally extending interface 1 can be formed between the first test component 2 and the second test component 3.

The test sample container 4 is depicted in a horizontal orientation for illustration purposes. Self-evidently, the test sample container 4 and the laboratory sample containers 4 depicted in FIG. 1 and the following figures are in fact oriented vertically, i.e., a longitudinal axis of the test container 4 can extend in a vertical direction denoted z during the execution of the disclosed method.

Figure 1B:
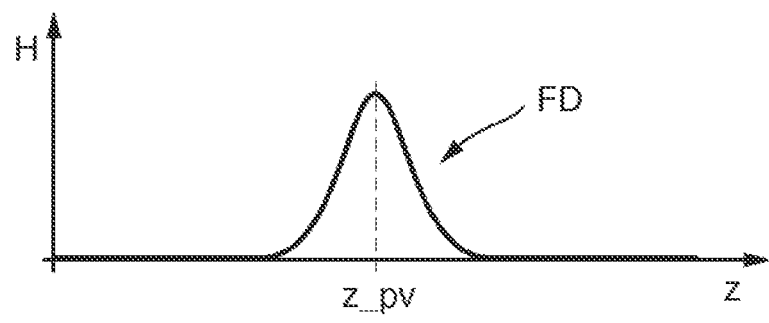
FIG. 1b illustrates a frequency distribution of a number of determined vertical positions of the horizontally extending interface depicted in FIG. 1a according to an embodiment of the present disclosure.

The vertical position z_pv of the horizontally extending interface 1 can be determined based on data generated by sensing a transmittance through the laboratory sample container 4 at different vertical positions z. The vertical position z_pv of the horizontally extending interface 1 can be repeatedly determined e.g., about 1000 times without changing the measuring setup or test setup. FIG. 1b depicts a resulting frequency distribution FD of the repeatedly determined vertical positions z_pv.

Figure 2A:
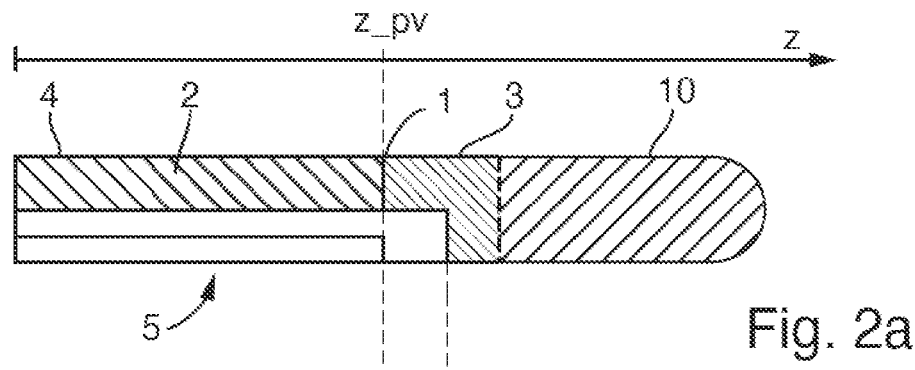
FIG. 2a illustrates a laboratory sample container containing a first component and a second component in layers that are vertically separated from each other, wherein a horizontally extending interface is formed between the first component and the second component, wherein a label is attached to the laboratory sample container according to an embodiment of the present disclosure.

FIG. 2a depicts a laboratory sample container 4 containing a centrifuged blood sample comprising a first component 2 in the form of blood serum, a second component 4 in the form of a gel and a third component 10 in the form of cruor in layers that are vertically separated from each other. A horizontally extending interface 1 can be formed between the first component 2 and the second component 3. A label 5 can be attached to the laboratory sample container 4.

Figure 2B:
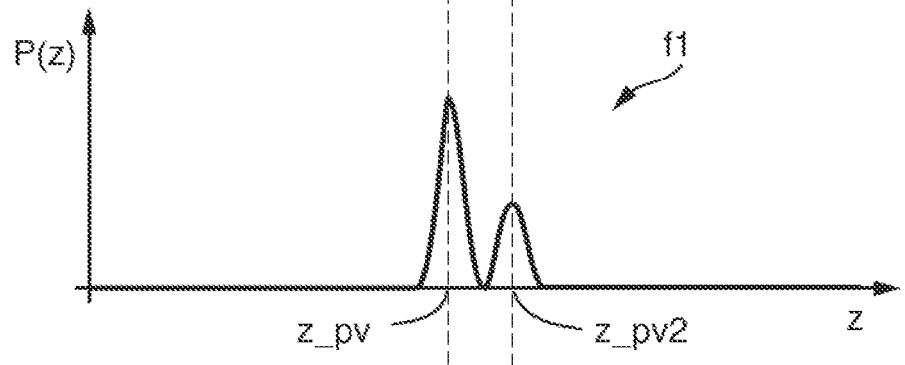
FIG. 2b illustrates a first probability distribution function, wherein the first probability distribution function assigns a probability of the presence of the horizontally extending interface depicted in FIG. 2a to a vertical position, wherein the first probability distribution function is determined in response to first data generated by sensing a transmittance through the laboratory sample container at different vertical positions, according to an embodiment of the present disclosure.

FIG. 2b depicts a first probability distribution function f1. The first probability distribution function f1 can assign a probability P(z) of the presence of the horizontally extending interface 1 depicted in FIG. 2a to a vertical position z. The first probability distribution function f1 can be determined in response to first data generated by sensing a transmittance through the laboratory sample container 4 at different vertical positions z as e.g., as disclosed in EP 2 770 317 A1.

To determine or calculate the first probability distribution function f1, the first data can be evaluated. Two vertical positions z_pv and z_pv2 can be extracted as likely interface positions. The vertical position z_pv can correspond to the true vertical position of the interface 1. The vertical position z_pv2 can correspond to the vertical position of the vertical boarder of the label 5, nevertheless having a reduced probability compared to the position z_pv. The vertical boarder of the label 5 can cause a change in transmission, potentially causing a false positive detected interface.

After having computed the two vertical positions z_pv and z_pv2 as likely interface positions, the frequency distribution FD depicted in FIG. 1b can be weighted with the probability at the corresponding positions z_pv and z_pv2 and can be centered at the positions z_pv and z_pv2, respectively.

Figure 2C:
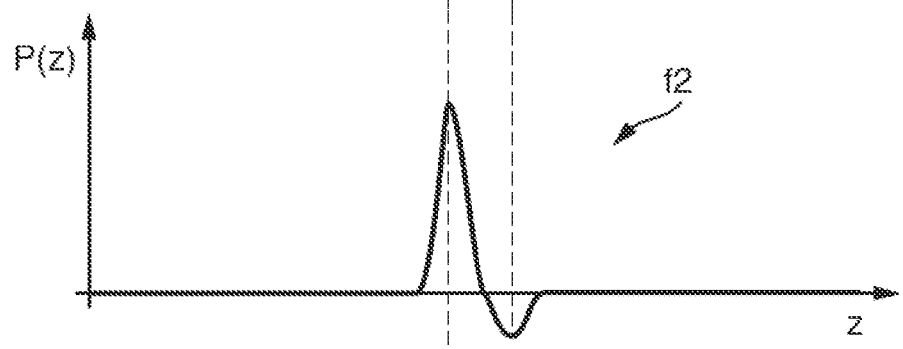
FIG. 2c illustrates a second probability distribution function, wherein the second probability distribution function assigns a probability of the presence of the horizontally extending interface depicted in FIG. 2a to a vertical position, wherein the second probability distribution function is determined in response to second data in form of picture data of the laboratory sample container according to an embodiment of the present disclosure.

FIG. 2c depicts a second probability distribution function f2. The second probability distribution function f2 can assign a probability of the presence of the horizontally extending interface 1 depicted in FIG. 2a to a vertical position z. The second probability distribution function f2 can be determined in response to second data in the form of picture data of the laboratory sample container and its content.

The second data can be evaluated by image processing extracting the vertical position z_pv of the interface 1 and the vertical position z_pv2 of the vertical boarder of the label 5. A frequency distribution describing the variation in extracting the position of the interface 1 and the geometrical properties of the label can be weighted with the probability at the corresponding positions z_pv and z_pv2 and centered at the positions z_pv and z_pv2, respectively. Finally, the values can be transformed into corresponding probabilities. In the range of the position z_pv, the probability of the presence of the horizontally extending interface 1 can be positive having a maximum value at the position z_pv. In the range of the position z_pv2, the probability of the presence of the horizontally extending interface 1 can be negative having a minimum value at the position z_pv2. Self-evidently, the negative values of the function f2 may not represent negative probabilities. Instead, the negative values can be arithmetical values denoting an unlikely interface position.

To finally determine the vertical position z_pv of the horizontally extending interface 1, the first probability distribution function f1 and on the second probability distribution function f2 can be combined, e.g., based on Bayes' theorem.

For example, using Gaussian distribution as probability distribution functions, the combined standard deviation $\sigma_{comb}$ can be calculated from the individual standard deviations from the individual measurements (first data and second data) $\sigma_i$ as $$\frac{1}{\sigma_{comb}^2} = \sum_{i=1}^{n} \frac{1}{\sigma_i^2}$$

wherein n is the number of used Gaussian-distribution or sensors. Therefore also n>2 sensors or distributions form image processing apparatus can be used to decrease the uncertainty of the measurement.

Since the vertical position z_pv of the horizontally extending interface 1 can be determined based on two different probability distribution functions f1 and f2. The probability distribution functions f1 and f2 can be based on different sensors, a performant sensor fusion can be achieved providing a more reliable interface detection compared to a solution using only one kind of sensor, i.e., transmission based sensor or a camera based sensor.

Figure 3A:
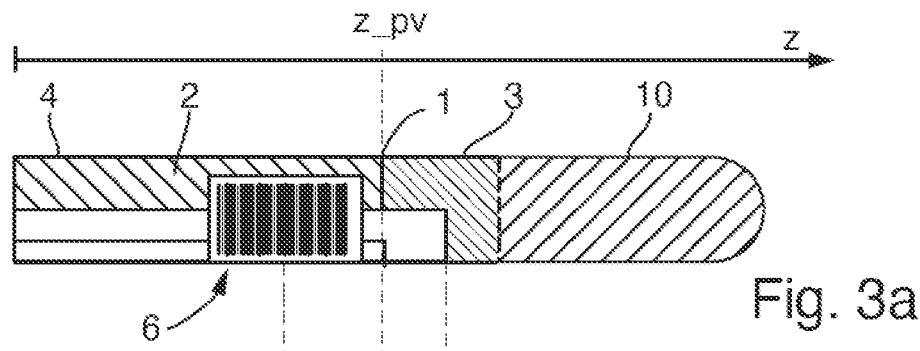
FIG. 3a illustrates a laboratory sample container containing a first component and a second component in layers that are vertically separated from each other, wherein a horizontally extending interface is formed between the first component and the second component, wherein a label and a barcode label are attached to the laboratory sample container according to an embodiment of the present disclosure.
Figure 3B:
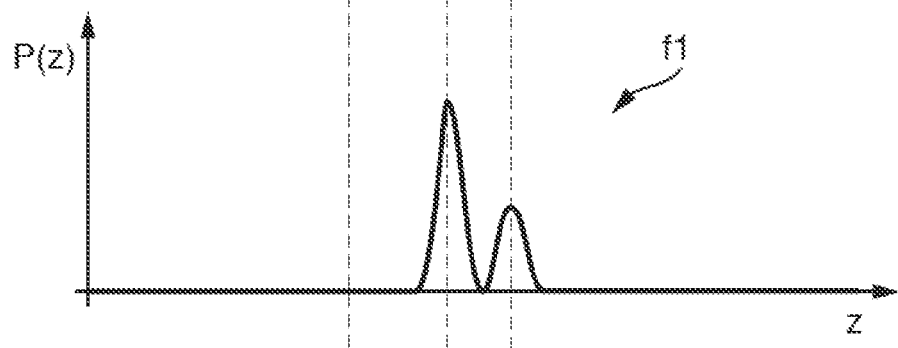
FIG. 3b illustrates a first probability distribution function, wherein the first probability distribution function assigns a probability of the presence of the horizontally extending interface depicted in FIG. 3a to a vertical position, wherein the first probability distribution function is determined in response to first data generated by sensing a transmittance through the laboratory sample container at different vertical positions according to an embodiment of the present disclosure.
Figure 3C:
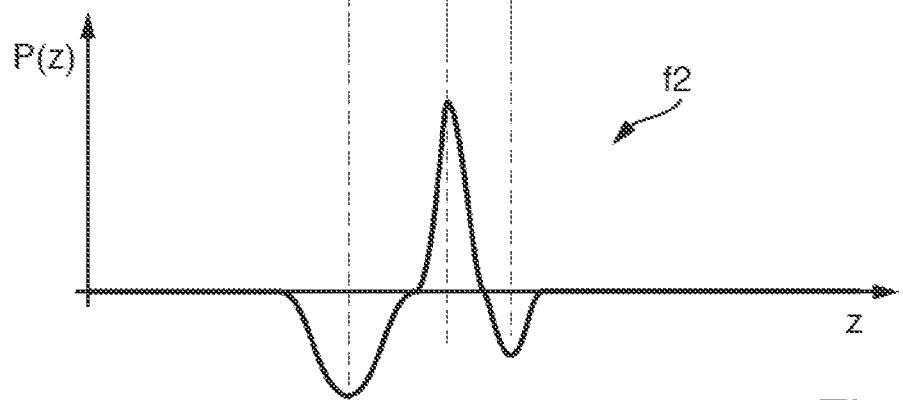
FIG. 3c illustrates a second probability distribution function, wherein the second probability distribution function assigns a probability of the presence of the horizontally extending interface depicted in FIG. 3a to a vertical position, wherein the second probability distribution function is determined in response to second data in form of picture data of the laboratory sample container according to an embodiment of the present disclosure.

In the embodiment depicted in FIGS. 3a-c, an additional barcode label 6 can be attached to the laboratory sample container 4. The first probability distribution function f1 can be computed as mentioned above. The barcode label 6 can be detected by image processing. The second probability distribution function f2 can denote unlikely probabilities in the range of the barcode label 6.

For instance, a normalized Gaussian distribution with negative values can be placed with the center in the center of the barcode and a 3σ width with the width of the barcode. The negative Gaussian distribution can be normalized to values between about 0.1 and about 0.8 such as, for example, between about 0.3 or about 0.5. This value can be deduced form the generated model, i.e., depending on how often the label edge coincides with the serum-separator/air interface. Alternatively, a constant negative probability with a value between 0 and 1 such as, for example, 0.5, 0.75 or 0.9 can be assigned along the barcode area.

Figure 4A:
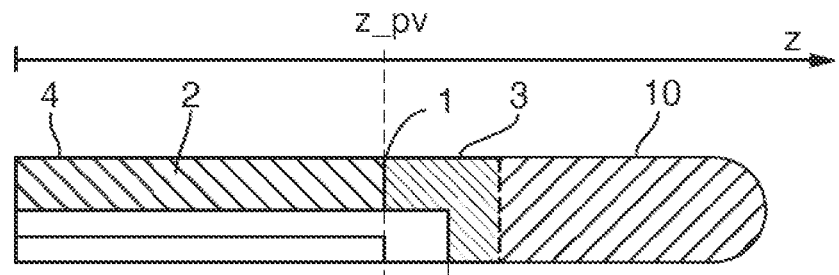
FIG. 4a illustrates a laboratory sample container containing a first component and a second component in layers that are vertically separated from each other, wherein a horizontally extending interface is formed between the first component and the second component, wherein a label is attached to the laboratory sample container according to an embodiment of the present disclosure.
Figure 4B:
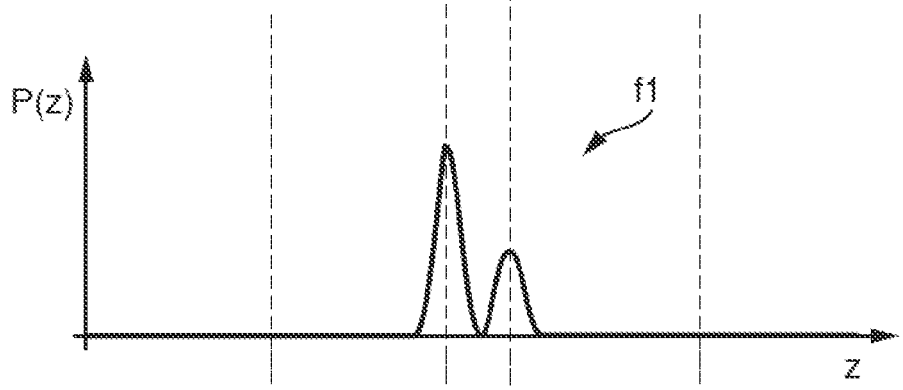
FIG. 4b illustrates a first probability distribution function, wherein the first probability distribution function assigns a probability of the presence of the horizontally extending interface depicted in FIG. 4a to a vertical position, wherein the first probability distribution function is determined in response to first data generated by sensing a transmittance through the laboratory sample container at different vertical positions according to an embodiment of the present disclosure.
Figure 4C:
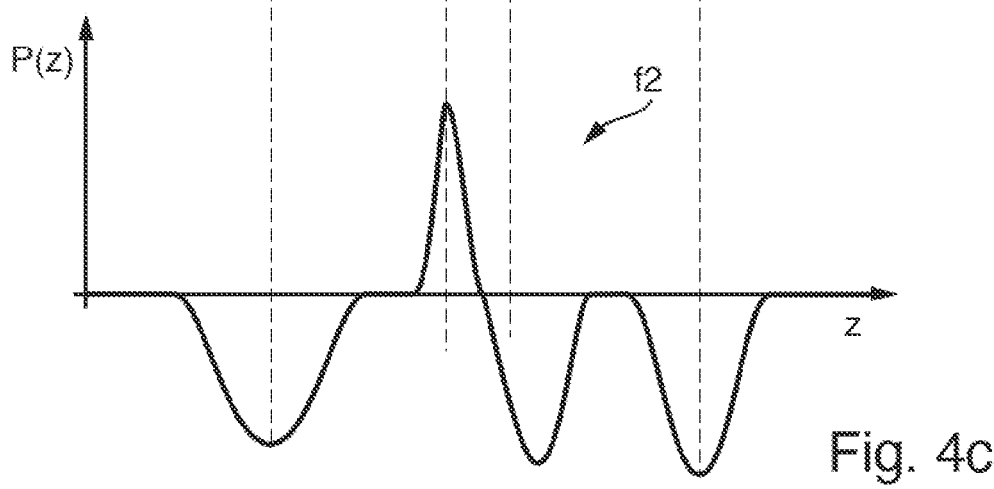
FIG. 4c illustrates a second probability distribution function, wherein the second probability distribution function assigns a probability of the presence of the horizontally extending interface depicted in FIG. 4a to a vertical position, wherein the second probability distribution function is determined in response to second data in form of picture data of the laboratory sample container according to an embodiment of the present disclosure.

In the embodiment depicted in FIGS. 4a-c, the second probability distribution function f2 can be generated additionally based on color information in the second date. As depicted, if no color change occurs, the probability of the occurrence of an interface can be reduced.

In addition, different probabilities can be assigned to different color changes. For instance for a color change between air (transparent) and serum (e.g., light yellow), a positive probability distribution according to the resolution of the measurement principle, e.g., camera resolution can be assigned to the interface. Also between serum and separation medium (almost white or blue or whatever color the separation medium has), a positive probability distribution can be assigned centered around the color change. The color of the separation medium can be identified by image processing of the whole tube by identifying the type of the tube according to one or several or all of the length and width of the tube and the form and color of the cap as well as the color of the liquid inside the tube. On the other hand, a negative distribution can be assigned to a color change between separation medium and blood clot (dark red).

Figure 5:
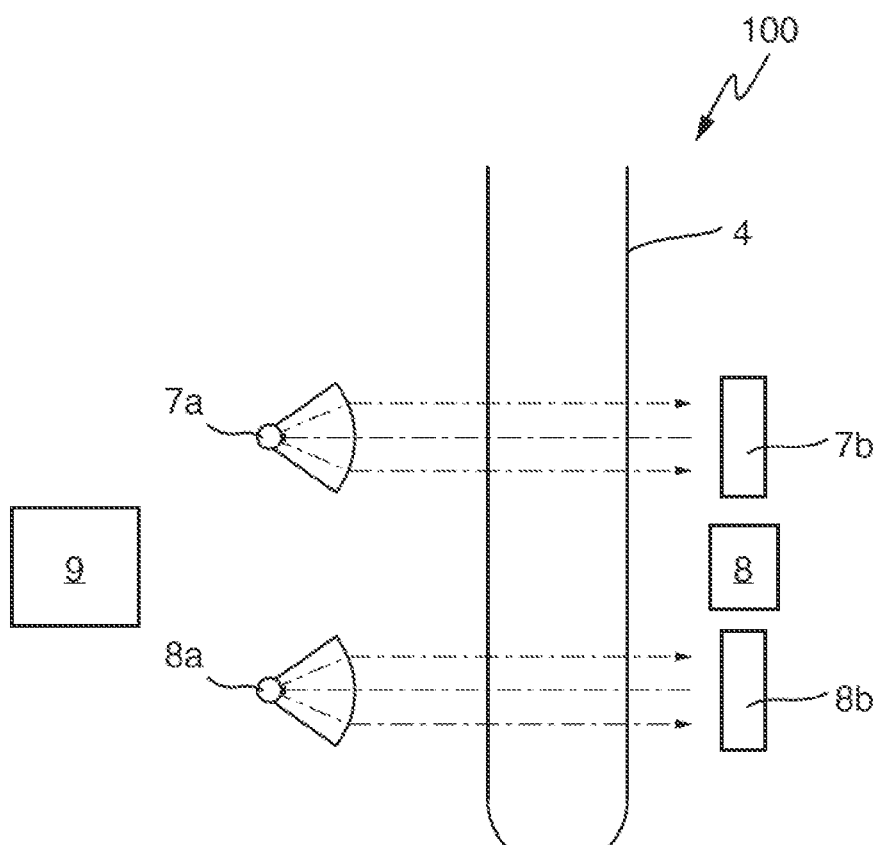
FIG. 5 illustrates highly schematic an apparatus for determining a vertical position of a horizontally extending interface between a first component and a second component according to an embodiment of the present disclosure.

FIG. 5 depicts an apparatus for performing the method as described above. The apparatus 100 can comprise a measurement unit 7a-b, 8a-b configured to generate the first data in the form of transmission data. The first data can depend on the vertical position z_pv of the horizontally extending interface 1.

The apparatus can further comprise a camera 8 configured to generate the second data in the form of picture data of the laboratory sample container 4 containing the first component 2 and the second component 3.

The apparatus can further comprise a processing unit 9 configured to execute the disclosed method.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for determining a vertical position (z_pv) of a horizontally extending interface between a first component and a second component, wherein the first component and the second component are contained in a laboratory sample container in layers that are vertically separated from each other, the method comprising:
   a. generating first data, wherein the first data depend on the vertical position (z_pv) of the horizontally extending interface;
   b. generating second data in the form of picture data of the laboratory sample container containing the first component and the second component;
   c. determining a first probability distribution function (f1) in response to the first data, wherein the first probability distribution function (f1) assigns a probability of the presence of the horizontally extending interface to a vertical position (z);

d. determining a second probability distribution function (f2) in response to the second data, wherein the second probability distribution function (f2) assigns a probability of the presence of the horizontally extending interface to a vertical position (z);

e. determining the vertical position (z_pv) of the horizontally extending interface depending on the first probability distribution function (f1) and on the second probability distribution function (f2);

f. repeating steps a.-e. to determine a vertical position (z_pv) of a horizontally extending interface a number of times;

g. determining a first frequency distribution (FD) of the determined vertical positions (z_pv); and h. determining the first probability distribution function (f1) in response to the first data and in response to the first frequency distribution (FD).

2. The method according to claim 1, wherein the first data are generated by sensing a transmittance through the laboratory sample container at different vertical positions (z).

3. The method according to claim 1, wherein the step of determining the vertical position (z_pv) of the horizontally extending interface depending on the first probability distribution function (f1) and on the second probability distribution function (f2) is performed by combining the first probability distribution function (f1) and the second probability distribution function (f2) based on Bayes' theorem and/or Dempster-Shafer theory and/or Kalman filtering.

4. The method according to claim 1, further comprising, providing a test sample container having a label attached to the test sample container;
determining geometrical properties of the label a number of times;
determining a second frequency distribution of the determined geometrical properties, and
determining the second probability distribution function (f2) in response to the second data and in response to the second frequency distribution.

5. The method according to claim 1, further comprising, providing a test sample container having a barcode label attached to the test sample container;
determining geometrical properties of the barcode label a number of times;
determining a third frequency distribution of the determined geometrical properties; and
determining the second probability distribution function (f2) in response to the second data and in response to the third frequency distribution.

6. The method according to claim 1, further comprising, generating the second data comprising color information, wherein the second probability distribution function (f2) is determined in response to the color information.

7. An apparatus for determining a vertical position (z_pv) of a horizontally extending interface between a first component and a second component, wherein the first component and the second component are contained in a laboratory sample container in layers that are vertically separated from each other, the apparatus comprising:
a measurement unit configured to generate first data, wherein the first data depend on the vertical position (z_pv) of the horizontally extending interface;
a camera configured to generate second data in the form of picture data of the laboratory sample container containing the first component and the second component; and
a processing unit configured to:
determine a first probability distribution function (f1) in response to the first data, wherein the first probability distribution function (f1) assigns a probability of the presence of the horizontally extending interface to a vertical position (z),
determine a second probability distribution function (f2) in response to the second data, wherein the second probability distribution function (f2) assigns a probability of the presence of the horizontally extending interface to a vertical position (z), and
determine the vertical position (z_pv) of the horizontally extending interface depending on the first probability distribution function (f1) and on the second probability distribution function (f2),
determine a vertical position (z_pv) of the horizontally extending interface between the first test component and the second test component based on data generated by sensing a transmittance through the laboratory sample container at different vertical positions a number of times,
determine a first frequency distribution (FD) of the determined vertical positions (z_pv), and
determine the first probability distribution function (f1) in response to the first data and in response to the first frequency distribution (FD).

8. The apparatus according to claim 7, wherein the measurement unit is configured to generate the first data by sensing a transmittance through the laboratory sample container at different vertical positions (z).

9. The apparatus according to claim 7, wherein the apparatus is configured to perform a method according to claim 1.

10. A method for determining a vertical position (z_pv) of a horizontally extending interface between a first component and a second component, wherein the first component and the second component are contained in a laboratory sample container in layers that are vertically separated from each other, the method comprising:
providing a test sample container, wherein the first test component and the second test component are contained in the test sample container in layers that are vertically separated from each other, generating first data, wherein the first data depend on the vertical position (z_pv) of the horizontally extending interface;
generating second data in the form of picture data of the laboratory sample container containing the first component and the second component;
determining a first probability distribution function (f1) in response to the first data, wherein the first probability distribution function (f1) assigns a probability of the presence of the horizontally extending interface to a vertical position (z);
determining a second probability distribution function (f2) in response to the second data, wherein the second probability distribution function (f2) assigns a probability of the presence of the horizontally extending interface to a vertical position (z); and
determining the vertical position (z_pv) of the horizontally extending interface depending on the first probability distribution function (f1) and on the second probability distribution function (f2), determining a vertical position (z_pv) of a horizontally extending interface between the first test component and the second test component based on data generated by sensing a transmittance through the laboratory sample container at different vertical positions a number of times, determining a first frequency distribution (FD) of the determined vertical positions (z_pv), determining the first probability distribution function (f1) in response to the first data and in response to the first frequency distribution (FD), and determining the vertical position (z_pv) of the horizontally extending interface from the first probability distribution function (f1) and the first frequency distribution (FD).

* * * * *